(12) United States Patent
Fukada et al.

(10) Patent No.: US 9,463,980 B2
(45) Date of Patent: Oct. 11, 2016

(54) METHOD FOR MANUFACTURING COKE

(71) Applicant: JFE STEEL CORPORATION, Chiyoda-ku, Tokyo (JP)

(72) Inventors: Kiyoshi Fukada, Fukuyama (JP); Hiroyuki Sumi, Kawasaki (JP); Izumi Shimoyama, Kurashiki (JP); Takashi Anyashiki, Kawasaki (JP); Hidekazu Fujimoto, Kawasaki (JP); Tetsuya Yamamoto, Fukuyama (JP); Yusuke Dohi, Fukuyama (JP)

(73) Assignee: JFE Steel Corporation, Tokyo (JP)

( * ) Notice: Subject to any disclaimer, the term of this patent is extended or adjusted under 35 U.S.C. 154(b) by 134 days.

(21) Appl. No.: 14/351,745

(22) PCT Filed: Oct. 11, 2012

(86) PCT No.: PCT/JP2012/006526
§ 371 (c)(1),
(2) Date: Oct. 13, 2014

(87) PCT Pub. No.: WO2013/054526
PCT Pub. Date: Apr. 18, 2013

(65) Prior Publication Data
US 2015/0047961 A1 Feb. 19, 2015

(30) Foreign Application Priority Data

Oct. 14, 2011 (JP) .................. 2011-226496

(51) Int. Cl.
| | | |
|---|---|---|
| C10B 57/04 | (2006.01) |
| C10B 57/08 | (2006.01) |
| C10B 53/04 | (2006.01) |
| C10B 53/08 | (2006.01) |
| C01B 31/02 | (2006.01) |
| C10L 5/36 | (2006.01) |

(52) U.S. Cl.
CPC ............... *C01B 31/02* (2013.01); *C10B 57/04* (2013.01); *C10B 53/04* (2013.01); *C10B 53/08* (2013.01); *C10B 57/08* (2013.01); *C10L 5/363* (2013.01); *C10L 5/366* (2013.01)

(58) Field of Classification Search
CPC ....... C10B 57/08; C10B 53/04; C10B 53/08; C10L 5/363; C10L 5/366
See application file for complete search history.

(56) References Cited

FOREIGN PATENT DOCUMENTS

| JP | 8-176553 A | 7/1996 |
| JP | 9-255966 A | 9/1997 |
| JP | 2002-294250 A | 10/2002 |
| JP | 2005-281355 A | 10/2005 |
| JP | 2008069258 | 3/2008 |

OTHER PUBLICATIONS

CoalTech, "Coke Reactivity & Strength after Reaction", Aug. 30, 2007 (Date obtained from wayback machine), http://www.coaltech.com.au/CokeReactivity&StrengthafterReaction.html.*

(Continued)

*Primary Examiner* — Renee E Robinson
*Assistant Examiner* — Jonathan Pilcher
(74) *Attorney, Agent, or Firm* — RatnerPrestia

(57) ABSTRACT

Coke is manufactured by blending two or more kinds of coal to form a coal blend and by carbonizing the coal blend. Interfacial tension among coal kinds is used as a control index for determining the blending ratio of each coal when forming the coal blend. It is possible to increase the strength of coke without increasing the material cost of a coal blend.

26 Claims, 3 Drawing Sheets

(56) References Cited

OTHER PUBLICATIONS

K.L Johnson, K. Kendall, and A.D. Roberts, "Surface Energy and the Contact of Elastic Solids", Sep. 8, 1971, Procedings of the Roayl Society of London. Series A, Mathematical and Physical Sciences, vol. 324, No. 1559, pp. 301-313.*

Diez et al., "Coal for metallurgical coke production: predictions of coke quality and future requirements for cokemaking", 2002, International Journal of Coal Geology 50, p. 389-412.*

International Search Report dated Nov. 6, 2012, application No. PCT/JP2012/006526.

European Search Report mailed Mar. 20, 2015 for European Application No. 12839478.0.

Forrest et al., "Theoretical and Experimental Approaches to the Carbonization of Coal and Coal Blends," Analytical Characterization Techniques, Nov. 12, 1982, vol. 205, pp. 1-25.

Oh et al., "An experimental and modeling study of softening coal pyrolysis," Aiche Journal, vol. 35, No. 5, May 1, 1989, pp. 775-792.

Dash et al,. "Laboratory scale investigation on maximising utilisation of carbonaceous inerts in stamp charging to improve coke quality and yield," Ironmaking & Steelmaking, vol. 34, No. 1, Jan. 1, 2007, pp. 23-29.

J.K. Spelt and D. Li; "The equation of state approach to interfacial tensions, in Applied Surface Thermodynamics", A.W. Neumann and J.K. Spelt (Eds); Advances in Chemistry Series, vol. 63, Marcel Dekker, New York, 1996, p. 239-292.

D.W. Fuerstenau; "International Journal of Mineral Processing, 20", 1987, p. 153-157.

* cited by examiner

METHOD FOR MANUFACTURING COKE

CROSS-REFERENCE TO RELATED APPLICATIONS

This is the U.S. National Phase application of PCT International Application No. PCT/JP2012/006526, filed Oct. 11, 2012, and claims priority to Japanese Patent Application No. 2011-226496, filed Oct. 14, 2011, the disclosures of each of these applications being incorporated herein by reference in their entireties for all purposes.

FIELD OF THE INVENTION

The present invention relates to a method for manufacturing high strength blast furnace coke.

BACKGROUND OF THE INVENTION

Blast furnace coke is used as a reducing agent, a heat resource, and a supporting material in order to keep gas permeability in a blast furnace. Nowadays, there is a trend toward manufacturing high strength coke so as to realize stable operation under the condition of a low reducing agent rate. Since plural kinds (ten kinds or more) of coal are typically blended and used when blast furnace coke is manufactured, investigations regarding a method for predicting the strength of coke which is derived from a coal blend have been conducted. For example, methods (A) through (C) below are well known.

(A) Coke Strength Prediction Method Using the Strength of Coke Matrix and Fluidity as Indices This method is based on a blending theory which predicts coke strength using two indices, which are a mean maximum reflectance of vitrinite (the average value of Ro, hereinafter, simply represented by Ro) and a Gieseler maximum fluidity (MF), as parameters for coal quality and is generally used nowadays.

(B) Coke Strength Prediction Method Using NMR

This is a coke strength prediction method using an index indicating the amount of coal plastic component which is determined using NMR (Nuclear Magnetic Resonance) and an index indicating the viscosity of coal plastic component (for example, refer to Patent Literature 1).

(C) Coke Strength Prediction Method Using a Blending Effect Coefficient as an Index The properties of coal vary depending on an origin, a coal mine, and a coal seam, and it is pointed out that there is compatibility among different kinds of coal when different kinds of coal are blended and used to manufacture coke.

In the cases of typical coke strength prediction equations used in the methods such as those described in (A) and (B) above, since the strength of coke which is derived from coal blend consisting of two kinds of coal is predicted using weighted average values of various physical properties, there are many cases where an effect of increasing strength due to compatibility, that is, a blending effect is not predicted. On the contrary, a method for predicting a blending effect is known. According to the method, the property of coke which is derived from coal blend consisting of plural kinds of coal is predicted on the assumption that the coke is the aggregation of all the combinations of two kinds of coal selected from among the constituent coal kinds of the coke, the difference between the property of coke derived from two kinds of coal and the weighted average value of the properties of the two kinds of coke which are respectively derived from the two kinds of single coal is represented by a blending effect coefficient, and a coke strength predicting equation is obtained using the blending effect coefficients (for example, refer to Patent Literature 2). A blending effect coefficient may be obtained by actual measurement or presumption.

Patent Literature

[PTL 1] Japanese Unexamined Patent Application Publication No. 2002-294250
[PTL 2] Japanese Unexamined Patent Application Publication No. 9-255966

Non Patent Literature

[NPL 1] J. K. Spelt and D. Li; "The equation of state approach to interfacial tensions, in Applied Surface Thermodynamics", A. W. Neumann and J. K. Spelt (Eds); Advances in Chemistry Series, vol. 63, Marcel Dekker, New York, 1996, p. 239-292.
[NPL 2] D. W. Fuerstenau; "International Journal of Mineral Processing, 20", 1987, p. 153.

SUMMARY OF THE INVENTION

Although, as coke strength prediction methods in order to manufacture high strength coke, the methods described above are proposed, coal having a high mean maximum reflectance of vitrinite (Ro) and a high Gieseler maximum fluidity (MF) is necessary to manufacture high strength coke using the method described in (A). Since this kind of coal is expensive, there is a problem of an increase in cost. In addition, in the case where non- or slightly-caking coal which is poor in fluidity is used, since there is a decrease in detection sensitivity for an index indicating fluidity, it is difficult to determine fluidity and there is a problem in that the determined value is not useful.

In addition, since the method described in (B) focuses on the fluidity and viscosity of coal which are indices having improved detection sensitivity for maximum fluidity (MF) in a practical sense, there is a problem regarding cost as is the case with the method described in (A). In addition, an apparatus to be used in the method described in (B) is expensive, special, and inconvenient.

Moreover, it is possible to predict coke strength more precisely using the method described in (C) in which a blending effect coefficient is used. However, since a parameter of a conventional coke strength equation is used in this method, this method is still not superior to conventional methods, which results in the problem regarding cost being left to be solved. In addition, although the interaction among coal particles is estimated in this method, since it is not an estimation based on a physical property regarding the adhesiveness of coal particles, the prediction precision of strength is not sufficiently good and there is a problem in that there is inconvenience in the case where a blending effect coefficient is obtained by practical measurement.

The present invention has been completed in order to solve the problems described above, and the present invention aims to provide a method for manufacturing coke by which it is possible to increase coke strength while preventing an increase in the material cost of raw coal.

The characteristics of the present invention which has been completed in order to solve the problems described above include the following.

(1) A method for manufacturing coke in which a coal blend is formed by blending two or more kinds of coal and the coal blend is carbonized, the method including using interfacial tension among the kinds of coal as a control index for determining the blending ratio of each kind of coal when forming the coal blend.

(2) The method for manufacturing coke according to item (1), the method further including: obtaining the interfacial tension among the kinds of coal using surface tension of each kind of coal, deriving in advance the relationship between the interfacial tension of a coal blend consisting of two or more kinds of coal and the strength of coke which is manufactured by carbonizing the coal blend, and determining the blending ratio of each kind of coal using the relationship such that the interfacial tension of the coal blend is within a range in which the coke has a desired strength.

(3) The method for manufacturing coke according to item (2), in which the surface tension of the coal is obtained by heating the coal at a temperature of an initial softening temperature or more and a solidification temperature or less, by cooling the heated coal under an inert gas atmosphere, and by performing measurement using the cooled coal.

(4) The method for manufacturing coke according to item (3), in which the surface tension of the coal is obtained by heating the coal at a temperature of 350° C. or higher and 800° C. or lower, by cooling the heated coal under an inert gas atmosphere and by performing measurement using the cooled coal.

(5) The method for manufacturing coke according to any one of items (2) to (4), in which the interfacial tension among the kinds of coal is obtained by deriving interfacial tension $\gamma_{inter}$ from equation (1) below using the surface tension of each kind of coal:

[Math. 1]
$$\gamma_{inter} = W\Gamma W^t, \quad (1)$$
where $$\Gamma = \begin{pmatrix} \gamma_{11} & \gamma_{12} & \cdots & \gamma_{1j} & \cdots & \gamma_{1n} \\ \gamma_{21} & \gamma_{22} & & & & \vdots \\ \vdots & & \ddots & & & \vdots \\ \gamma_{i1} & & & \gamma_{ij} & & \gamma_{in} \\ \vdots & & & & \ddots & \vdots \\ \gamma_{n1} & \cdots & \cdots & \gamma_{nj} & \cdots & \gamma_{nn} \end{pmatrix}$$

$$\gamma_{ij} = \gamma_i + \gamma_j - 2\exp[-\beta(\gamma_i - \gamma_j)^2]\sqrt{\gamma_i\gamma_j}$$

$$\gamma_{ij} = \gamma_{ji}$$

$$W = (w_1 \; w_2 \; \cdots \; w_i \; \cdots \; w_n)$$

$$\sum_{i=1}^{n} w_i = 1$$

$\gamma_i$: the surface tension of coal i
$\gamma_{ij}$: the interfacial tension between coal i and coal j
$w_i$: the blending ratio of coal i
$\gamma_{inter}$: the interfacial tension of a coal blend consisting of coal 1, coal 2, ..., coal i, ... and coal n.

(6) The method for manufacturing coke according to any one of items (2) to (4), in which the interfacial tension among the kinds of coal is obtained by deriving interfacial tension $\gamma_{inter}$ from equation (2) below using the surface tension of each kind of coal:

[Math. 2]
$$\gamma_{inter} = 0.032\sigma_\gamma^2 \quad (2)$$

$$\sigma_\gamma^2 = \frac{100}{100\sum_{i=1}^{n} w_i - 1}\left[\sum_{i=1}^{n}\gamma_i^2 w_i - \frac{\left(\sum_{i=1}^{n}\gamma_i w_i\right)^2}{\sum_{i=1}^{n} w_i}\right]$$

$$\sum_{i=1}^{n} w_i = 1,$$

where
$\gamma_i$: the surface tension of coal i
$w_i$: the blending ratio of coal i
$\gamma_{inter}$: the interfacial tension of a coal blend consisting of coal 1, coal 2, ..., coal i, ... and coal n
$\sigma_\gamma^2$: the variance of the surface tensions of all the constituent kinds of coal.

(7) The method for manufacturing coke according to item (5) or (6), in which the blending ratio of each kind of coal is determined so that the interfacial tension $\gamma_{inter}$ is 0.03 mN/m or less.

(8) The method for manufacturing coke according to item (7), in which a coal blend having a weighted average value of Ro of the constituent kinds of coal of 0.90% or more and 1.30% or less and a weighted average value of log MF of the constituent kinds of coal of 2.3 or more and 2.8 or less is used, where Ro is a mean maximum reflectance and MF is a Gieseler maximum fluidity.

(9) The method for manufacturing coke according to item (5) or (6), in which the blending ratio of each kind of coal is determined so that the interfacial tension $\gamma_{inter}$ is 0.02 mN/m or less in the case of a coal blend having a weighted average value of Ro of the constituent kinds of coal of 0.90% or more and 1.30% or less and a weighted average value of log MF of the constituent kinds of coal of 2.0 or more and less than 2.3, where Ro is a mean maximum reflectance and MF is a Gieseler maximum fluidity.

(10) The method for manufacturing coke according to item (5) or (6), in which the blending ratio of each kind of coal is determined so that the interfacial tension $\gamma_{inter}$ is 0.01 mN/m or less in the case of a coal blend containing 30 mass % or more of coal having a log MF of 1.4 or less, where MF is a Gieseler maximum fluidity.

In the method according to the present invention, coke strength is predicted in consideration of adhesive strength due to the surface tension among coal particles, and the blending ratio of each kind of coal brand is determined by using this prediction method. That is to say, in the method according to the present invention, coke is manufactured by using indices other than those used in conventional methods. Therefore, there are effects as follows.

(a) Since there is an increase in the prediction precision of a coke strength prediction equation, it is possible to manufacture coke under blending conditions which cannot be found by using conventional parameters of coal properties.

(b) In addition, since there is an increase in parameters of coal properties which causes an increase in the freedom of purchasing materials, it is possible to increase coke strength without increasing material cost.

(c) Moreover, since the method according to the present invention can be applied to non- or slightly-caking coal whose fluidity is too low to evaluate using a Gieseler plastometer, it is possible to significantly increase the freedom of blending raw coal.

DETAILED DESCRIPTION OF EMBODIMENTS OF THE INVENTION

Figure 1:
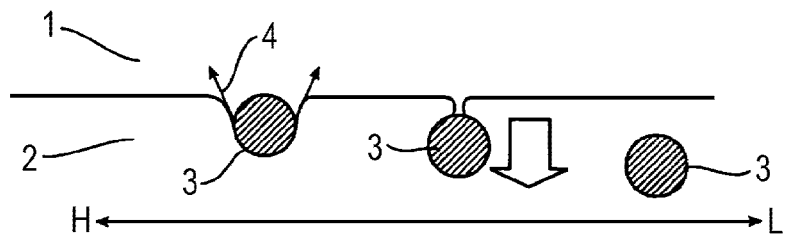
FIG. 1 is a diagram illustrating the principle of the measurement of surface tension using a film flotation method.

Coke is manufactured by carbonizing coal particles which soften and adhere to each other. Therefore, it is considered that adhesive strength among coal particles has an influence on coke strength.

Generally, adhesive strength among coal particles increases with a decrease of interfacial tension at adhesive interfaces. It can be considered that interfacial tension is a kind of free energy which is present at interfaces judging from the fact that interfacial tension is expressed in units of mN/m. Therefore, the fact that interfacial tension is present means that free energy which can cause force is present at interfaces. Therefore, large interfacial tension results in a tendency for a fracture to occur. Although, in the present invention, adhesive strength among coal particles is evaluated using interfacial tension as an index on the assumption that interfacial tension has an influence on adhesive strength among coal particles, there is a problem in that it is difficult to measure interfacial tension.

Although it is preferable that interfacial tension be directly measured at interface among coal particles of different coal brands, it is very difficult in the case where conventional methods are used. Therefore, in the present invention, a method for predicting interfacial tension on the basis of the surface tension of each kind of coal brand is utilized as described below, and the blending ratio of coal is determined using the interfacial tension. However, there were things which were left to be clarified such as measurement conditions for surface tension which can be suitably used for predicting coke strength, a method for predicting interfacial tension using surface tension, and the degree of influences of these factors on coke strength. The present inventors conducted investigations regarding these factors, found a method effective for predicting coke strength, and completed the present invention.

Interfacial tension can be derived from the surface tension of the materials which contact with each other. Regarding different materials A and B, interfacial tension between the materials A and B can be derived from the surface tension of each of materials A and B, and, for example, the interfacial tension can be derived from equation (3) below using a Girifalco-Good equation.

[Math. 3]

$$\gamma_{AB} = \gamma_A + \gamma_B - 2\phi\sqrt{\gamma_A \gamma_B} \quad (3)$$

Here, $\gamma_A$, $\gamma_B$: the surface tensions of materials A and B, $\gamma_{AB}$: interfacial tension between materials A and B, and $\phi$: interaction coefficient. $\phi$ can be experimentally obtained and it is known that the value of $\phi$ varies between materials A and B.

In addition, D. Li and A. W. Neumann propose equation (4) below which is derived by modifying equation (3) on the assumption that $\phi$ increases as difference between $\gamma_A$ and $\gamma_B$ increases.

[Math. 4]

$$\gamma_{AB} = \gamma_A + \gamma_B - 2\exp[-\beta(\gamma_A - \gamma_B)^2]\sqrt{\gamma_A \gamma_B} \quad (4)$$

Here, $\beta$: constant. $\beta$ is experimentally derived, and D. Li and A. W. Neumann derived a calculated value of 0.0001247 $(m^2/mJ)^2$ for $\beta$ (refer to Non Patent Literature 1). Therefore, interfacial tension between coal A and coal B can be derived by measuring the surface tensions of coal A and coal B and by substituting these into equation (3) or (4). Since it is necessary that $\phi$ be experimentally obtained in the case where equation (3) is used, it is preferable that equation (4), in which the value of $\phi$ is predicted, be used in order to conveniently derive interfacial tension.

It is considered that adhesive strength among coal particles in a coking process is influenced by surface tension from the beginning of softening until the end of solidification. Therefore, it is preferable that surface tension of coal in the softened state be measured. However, it is difficult in practical operation to measure surface tension of coal when coal particles soften and adhere to each other. From the result of the investigations, the present inventors found that the surface tension of coal in the softened state can be predicted by heating, with air being shut off, coal up to a temperature at which coal softens, that is, heating coal in an inert atmosphere, cooling the heated coal at a cooling rate of 10° C./sec or more, and measuring the surface tension of the coal.

Since it is considered that surface tension has an influence on adhesion among coal particles, it is appropriate that the heating temperature described above is set to be in the range in which coal particles begin softening, adhere to each other, solidify, and finish coking process, that is, 350° C. or higher, at which coal particles begin softening, and 800° C. or lower, at which coking is finished. In the range of the heating temperature from 350° C. to 800° C., a temperature at which softening occurs in particular contributes to adhesion. Since a temperature range in which coal that is used for manufacturing coke softens is from 350° C. to 500° C. and it can be said that a temperature at which all kinds of coal soften is 500° C., it is preferable that the heating temperature be 480° C. to 520° C. in particular around 500° C. Further, since the surface tension of the heat treated coal has a correlation to some extent with the surface tension of the raw coal, it is also possible to derive interfacial tension using the surface tension of the coal.

The heat treated coal is rapidly cooled in order to keep a molecular structure in the softened state, and therefore it is preferable that the cooling rate be 10° C./sec or more at which it is considered that a molecular structure does not change. Examples of rapid cooling methods include one using liquefied nitrogen, iced water, water, or inert gas such as nitrogen. It is preferable to perform rapid cooling using liquefied nitrogen, because it takes time to cool inside a specimen and there are variations regarding the cooling rate in the case of using a gas cooling method, and because the measurement of surface tension is influenced by humidity which is present at the surface of a specimen in the case of cooling with iced water or water.

As methods for measuring surface tension, a sessile drop method, a capillary-rise method, a maximum bubble pressure method, a drop weight method, a pendant drop method, a ring method, a Whilhelmy method, an advancing/receding contact angle method, a tilting plate method, a film floatation method, and the like are known. Since coal consists of various molecular structures, and since it is supposed that coal has an uneven distribution of surface tension, it is in particular preferable that a film floatation method, by which it is expected to be possible to evaluate surface tension distribution (refer to Non Patent Literature 2), be used. A film floatation method is a method by which the surface tension of a solid body can be measured.

Figure 2:
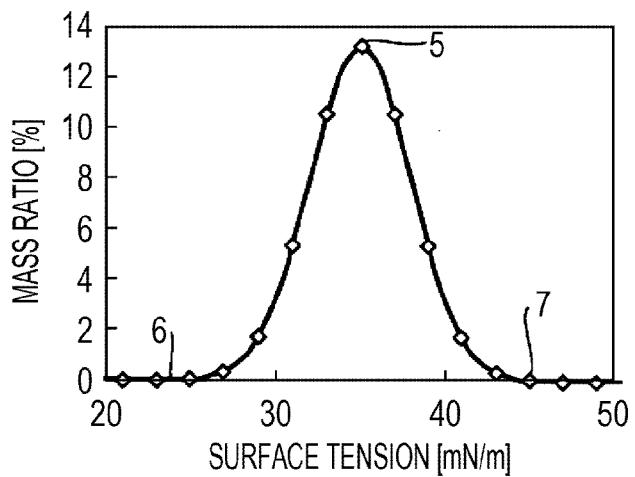
FIG. 2 is a graph illustrating surface tension distribution using a frequency distribution curve.

The basic principle of a film floatation method will be described in reference to FIG. 1. A film flotation method is based on the thought that, in the case where pulverized specimen particles 3 are dropped from a gas phase 1 onto the surface of liquid 2, the surface tensions of the specimen particle and the liquid are equal to each other when the specimen particle 3 is dipped just under the surface of the liquid 2 (in the case of the specimen particle located at the center of FIG. 1 where a contact angle is substantially 0°). Arrows 4 represent the direction of the surface tension of the specimen particle 3. A white arrow located at the center of FIG. 1 represents the dipping direction, and a horizontal arrow represents that the surface tension of the liquid is high is on the left side (H side) in the figure and the surface tension of the liquid is low on the right side (L side) in the figure. By dropping specimen particles onto various kinds of liquid having various surface tensions, obtaining the mass ratio of floating specimen particles for each kind of liquid, and representing the results in the form of a frequency distribution curve, the distribution curve of surface tension is derived as illustrated in FIG. 2. Here, surface tension which is directly derived by the film floatation method is a critical surface tension (the surface tension of the liquid when a contact angle is 0°), and the surface tension of coal can be derived from the critical surface tension as described below. Equation (5) below is derived from equation (3) above, where $\gamma_S$: the surface tension of a solid body (coal), $\gamma_L$: the surface tension of liquid, $\gamma_{SL}$: interfacial tension, $\gamma_C$: critical surface tension, and $\phi$: interaction coefficient (between coal and liquid).

$$\gamma_{SL} = \gamma_S + \gamma_L - 2\phi(\gamma_S\gamma_L)^{0.5} \tag{5}$$

Equation (6) is derived from Young's Equation.

$$\gamma_S = \gamma_L \cos\theta + \gamma_{SL} \tag{6}$$

Equation (7) is derived from equations (5) and (6).

$$1 + \cos\theta = 2\phi(\gamma_S/\gamma_L)^{0.5} \tag{7}$$

Equation (8) is derived by substituting $\theta=0°$ and $\gamma_L=\gamma_C$ into equation (7).

$$1 + 1 = 2\phi(\gamma_S/\gamma_C)^{0.5} \tag{8}$$

Equation (9) is derived by squaring both sides of equation (8).

$$\phi^2\gamma_S = \gamma_C \tag{9}$$

The surface tension $\gamma_S$ of coal can be derived from the critical surface tension $\gamma_C$ and $\phi$ in equation (9). Difference in structure between liquid used in a film flotation method and coal is large. As compared to the difference, it is considered that difference in structure among the kinds of coal (coal kinds) is small. Since an interaction coefficient $\phi$ is a parameter which is influenced by the molecular structures of relevant materials, surface tension $\gamma_S$ is represented only by the critical surface tension $\gamma_C$ on the assumption that the interaction coefficient $\phi$ is constant independently of coal brand. Therefore, it can also be said that the surface tension of coal can be evaluated only on the basis of a critical surface tension. In the present invention, on the assumption that the interaction coefficient $\phi$ is 1, it is considered that the value of the surface tension $\gamma_S$ of coal is equal to the critical surface tension $\gamma_C$.

Various conditions on a film flotation method will be described hereafter. Since the surface tension of coal or coal in the softened state is distributed in a range from 20 to 73 mN/m, it is appropriate that liquid having surface tension in this range is used as a liquid for the film flotation method. For example, it is possible to make liquid having a surface tension of 20 to 73 mN/m from aqueous solutions of organic solvents such as ethanol, methanol, propanol, tert-butanol, and acetone. Regarding the diameter of sample particles which are used to measure surface tension, since it is preferable that surface tension be measured when a contact angle is almost equal to 0° from the viewpoint of measurement principle, and since a contact angle increases with an increase in diameter of sample particles, it is preferable that the diameter be as small as possible. However, since the particles tend to aggregate in the case where the diameter of sample particles is less than 53 μm, it is preferable that the sample be pulverized so that the diameter of sample particles is 53 to 150 μm. In addition, since a film flotation method utilizes the flotation of a material due to surface tension, it is necessary that measurement be conducted under the condition that the gravity of the material is negligible. This is because there is an increase in contact angle due to the influence of gravity in the case where the density of the material is large. Therefore, it is preferable that the surface tension of a material having a density of 2000 kg/m³ or less with which it is considered that a contact angle is not influenced by gravity be measured. Since various kinds of coal satisfy this condition, it is possible to measure the surface tension of all kinds of coal such as hard coking coal, non- or slightly-caking coal, and anthracite regardless of the kinds of coal. Moreover, it is also possible to measure the surface tension of additives such as pitch, oil coke, coke breeze, dust, waste plastics, and biomass in the same way.

One of the examples of methods for preparing samples which is used for a film flotation method is a method in which sample is prepared by pulverizing coal to powder having a diameter of 200 μm or less, by heating the pulverized coal up to a temperature of 500° C. at a heating rate of 3° C./rain, by cooling the heat-treated coal with liquefied nitrogen, by pulverizing the cooled coal to powder having a diameter of 150 μm or less, and by drying the powder in a dried inert gas flow at a temperature of 120° C. for a duration of 2 hours, and this method may be used. It is preferable that the diameter of pulverized heat-treated coal be 250 μm or less as is specified as the diameter of pulverized coal in the proximate analysis of coal according to JIS M 8812 in order to make uniform sample from coal which is not uniform in coal macerals or properties. Although a heating rate is set to be 3° C./min because a heating rate when coke is manufactured in a coke oven is about 3° C./min, it is preferable that the heating rate is controlled in accordance with a heating rate at which coke whose surface tension is to be evaluated is heated in a practical manufacturing process. Any kind of drying method may be used as long as humidity which is present on the surface of sample particles can be removed, and a method in which drying is performed under reduced pressure may also be used other than the method in which heating is performed in an inert gas such as nitrogen or argon at a temperature of 100° C. to 200° C.

The reason why cooling is performed in an inert atmosphere after heating sample particles up to a temperature of about 500° C. is that it is intended to decrease the measurement error of surface tension. This is because, since the temperature of coal is high immediately after heating has been performed, there is a change in structure due to the partial oxidation of the coal surface in the case where cooling is performed in an atmosphere containing oxygen, which results in the measurement error of surface tension. The measurement results of surface tension using this method in different cooling atmospheres are given in Table 1. As shown in Table 1, cooling was performed on some heated coal only by changing a cooling atmosphere, and measurement was conducted twice (n=1, 2) for each atmosphere and the average value of the two measurement values were derived. Two kinds of cooling atmosphere were used, where one was atmospheric air (20° C.) and the other was nitrogen atmosphere (20° C.)

TABLE 1

|  | n | Mean Surface Tension [mN/m] | Difference |
|---|---|---|---|
| Atmospheric Air (20° C.) | 1 | 41.4 | 1.2 |
|  | 2 | 42.6 |  |
| Nitrogen Atmosphere (20° C.) | 1 | 40.1 | 0.3 |
|  | 2 | 40.4 |  |

Table 1 indicates that, although the difference between the results of the two measurements was as small as 0.3 in the case where cooling was performed in an inert atmosphere (20° C.), the difference between the results of the two measurements was as large as 1.2 in the case where cooling was performed in atmospheric air (20° C.). In consideration that the measurement error of this measuring method (the standard deviation of the measurement results with the same sample) is 0.4, it is preferable that cooling be performed in an inert atmosphere such as nitrogen gas in order to also decrease the variation of the measurement results of surface tension. Although a rare gas such as argon or nitrogen gas may be used for an inert atmosphere, nitrogen gas is typically used.

Examples of indices for representing the surface tension of a single coal brand (single coal) include the average value of surface tension distribution, the standard deviation of surface tension, the surface tension at the peak of surface tension distribution, the maximum and minimum values of surface tension distribution, and the distribution function of surface tension distribution. The average value of surface tension distribution (represented by γ with an overline) is expressed by, for example, equation (10) below.

[Math. 5]

$$\bar{\gamma} = \int \gamma f(\gamma) d\gamma \quad (10)$$

Here, γ: surface tension, f(γ): the frequency of surface tension distribution. The standard deviation of surface tension distribution ($\sigma_\gamma$) is expressed by, for example, equation (11).

[Math. 6]

$$\sigma_\gamma = [\int (\gamma - \bar{\gamma})^2 f(\gamma) d\gamma]^{0.5} \quad (11)$$

The surface tension at the peak of surface tension distribution and the minimum and maximum values of surface tension distribution are respectively represented by 5, 6, and 7 in FIG. 2. Examples of the distribution functions of surface tension include normal distribution, logarithmic normal distribution, F-distribution, chi-square distribution, exponential distribution, gamma distribution, and beta distribution, each of which has a form of distribution similar to surface tension distribution.

Regarding the timing of the measurement of surface tension, it is preferable to measure surface tension within 7 days before the day when a coal blend is prepared in order to manufacture coke, more preferably immediately before manufacturing coke, if possible. Since surface tension is influenced by a molecular structure, the measured value of surface tension may vary due to storing conditions of coal and weathering of coal. Therefore, it is preferable that the time between the measurement and the preparation be as short as possible. In addition, since surface tension of the same kind of coal may vary due to quality adjustment or the degree of blending at a coal mine, it is preferable that surface tension be measured every time coal arrives.

Figure 3:
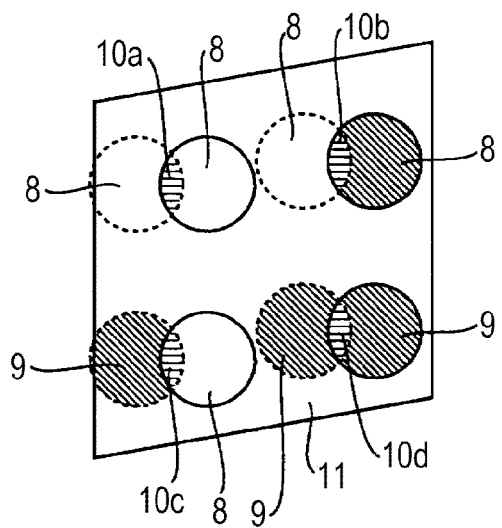
FIG. 3 is a schematic diagram illustrating some plane inside coke derived from a coal blend consisting of two kinds of coal in a ratio of 1:1.

An example case where the interfacial tension of a coal blend is derived using equation (4) using the average value of surface tension distribution derived from equation (10) as an index for representing surface tension will be described hereafter. Here, it is assumed that there are two kinds of coal A and B having different surface tensions. As illustrated in FIG. 3, in the case where coke is manufactured by uniformly blending coal A 8 and coal B 9 with a blending ratio of 1:1, it is considered that there are an interface 10a between particles of coal A 8, an interface 10d between particles of coal B 9, and interfaces 10b and 10c between particles of coal A 8 and coal B 9 in a certain plane 11 inside the coke. On the assumption that these interfaces are respectively named a-a interface, b-b interface, and a-b interface, it is necessary that the interfacial tension of coal A and coal B be derived by summarizing the values of interfacial tension of a-a interface, b-b interface, and a-b interface. Therefore, the interfacial tension of a coal blend consisting of coal A and coal B is defined by the sum of the products of interfacial tension and existence probability of all the interfaces. The specific calculation formula is expressed by equation (12) below.

$$\gamma_{AB} = p_{aa}\gamma_{aa} + p_{ab}\gamma_{ab} + p_{bb}\gamma_{bb} \quad (12),$$

where $\gamma_{AB}$: the interfacial tension of a coal blend consisting of coal A and coal B, $p_{aa}$: the existence probability of a-a interface, $p_{ab}$: the existence probability of a-b interface, $p_{bb}$: the existence probability of b-b interface, $\gamma_{aa}$: the interfacial tension of a-a interface, $\gamma_{ab}$: the interfacial tension of a-b interface, and $\gamma_{bb}$: the interfacial tension of b-b interface. It is assumed that the interfacial tension of each interface is derived by substituting the average values of the distributions of the surface tensions of coal A and coal B into equation (4). It is considered that the existence probability of each interface varies depending on the blending ratios of coal A and coal B. Therefore, it is assumed that the existence probability of each interface is derived from the products of blending ratios of coal A and coal B. The detail will be described hereafter.

a-a interface: calculated by multiplying the blending ratio of coal A by the blending ratio of coal A. Since coal A and coal B are blended with a blending ratio of 1:1, the blending ratios of coal A and coal B are both 50%. Therefore, the existence probability of the interface is 25% from equation (13) below.

$$0.5 \times 0.5 = 0.25 \quad (13)$$

a-b interface: calculated by multiplying the blending ratio of coal A by the blending ratio of coal B. It is assumed that a-b interface and b-a interface are the same. The existence probability of the interface is 50% from equation (14) below.

$$0.5 \times 0.5 + 0.5 \times 0.5 = 0.5 \quad (14)$$

b-b interface: calculated by multiplying the blending ratio of coal B by the blending ratio of coal B. The existence probability of the interface is 25% from equation (15) below.

$$0.5 \times 0.5 = 0.25 \quad (15)$$

By summarizing the description above, the calculation formula of interfacial tension is expressed by equation (16) below which is derived by replacing existence probability by blending ratio in equation (12).

$$\gamma_{AB} = w_a w_a \gamma_{aa} + w_b w_b \gamma_{bb} + 2 w_a w_b \gamma_{ab} \quad (16),$$

where $w_a$: the blending ratio of coal A and $w_b$: the blending ratio of coal b.

By extending this approach to a coal blend consisting of two or more kinds of coal, the relationship among the blending ratios of all the constituent kinds of coal is expressed by equation (17) below in the case where n kinds of coal are blended.

[Math. 7]

$$\sum_{i=1}^{n} w_i = 1 \quad (17)$$

Here, $w_i$: the blending ratios of coal 1, 2, ..., i, ... n. The existence probability of i-j interface between coal and coal j is expressed by the products of $w_i$ and $w_j$. Since the interfacial tension of a coal blend is defined by the sum of the products of the existence probability and interfacial tension of all the interfaces, the interfacial tension of a coal blend is expressed by equation (18).

[Math. 8]

$$\gamma_{inter} = \sum_{i=1}^{n} \sum_{j=1}^{n} w_i w_j \gamma_{ij} \quad (18)$$

Here, $\gamma_{inter}$: the interfacial tension of a coal blend. In addition, $$\gamma_{ij} = \gamma_{ji} \quad (19)$$

By rewriting equation (18) using matrices, equations (20) through (22) are derived.

Here, t is a symbol representing a transposed matrix.

[Math. 9]

$$\gamma = W \Gamma W^t \quad (20)$$

[Math. 10]

$$\Gamma = \begin{pmatrix} \gamma_{11} & \gamma_{12} & \cdots & \gamma_{1j} & \cdots & \gamma_{1n} \\ \gamma_{21} & \gamma_{22} & & & & \vdots \\ \vdots & & \ddots & & & \vdots \\ \gamma_{i1} & & & \gamma_{ij} & & \gamma_{in} \\ \vdots & & & & \ddots & \vdots \\ \gamma_{n1} & \cdots & & \gamma_{nj} & \cdots & \gamma_{nn} \end{pmatrix} \quad (21)$$

[Math. 11]

$$W = \begin{pmatrix} w_1 & w_2 & \cdots & w_n \end{pmatrix} \quad (22)$$

As described at the beginning, the adhesive strength of an interface increases with a decrease of interfacial tension. In equation (4), the condition under which $\gamma_{AB}$ is minimized is $$\gamma_A = \gamma_B \quad (23).$$

That is to say, in the case where the kinds of coal whose surface tensions are equal to each other are blended, interfacial tension is minimized. Therefore, it can be said that determining blending conditions under which interfacial tension is minimized using equation (20) is the same as determining blending conditions under which the differences among surface tensions of constituent kinds of coal are small.

Figure 4:
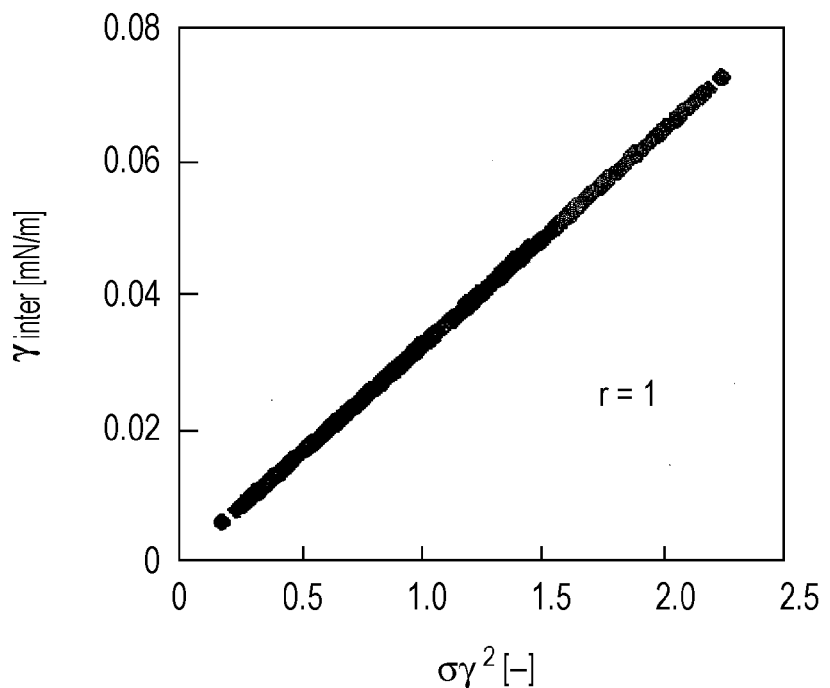
FIG. 4 is a graph illustrating the relationship between the variance of surface tension and the interfacial tension of constituent kinds of coal of a coal blend.

Moreover, the present inventors found a method for predicting the interfacial tension of a coal blend by using the variance of the surface tensions of all the constituent kinds of coal instead of using equation (20). This method is based on utilizing the fact that there is a strong correlation between the interfacial tension derived from equation (20) and the variance of the surface tensions of all the constituent kinds of coal in the case of coal blends which have been used in practical operation in the past two years. The correlation is illustrated in FIG. 4. In addition, the formula for calculating the variance of the surface tensions of all the constituent kinds of coal is expressed by equation (24), and the correlation equation is expressed by equation (25).

[Math. 12]

$$\sigma_\gamma^2 = \frac{100}{100 \sum_{i=1}^{n} w_i - 1} \left[ \sum_{i=1}^{n} \gamma_i^2 w_i - \frac{\left( \sum_{i=1}^{n} \gamma_i w_i \right)^2}{\sum_{i=1}^{n} w_i} \right] \quad (24)$$

[Math. 13]

$$\gamma_{inter} = 0.032 \sigma_\gamma^2 \quad (25)$$

Here, $\sigma_\gamma^2$: the variance of the surface tensions of all the constituent kinds of coal, $\gamma_i$: the surface tensions of coal 1, 2, ..., i, ... n, $w_i$: the blending ratios of coal 1, 2, ..., i, ... n which satisfy equation (17). A spreadsheet software is often used in order to calculate blending conditions in practical operation. However, since matrix calculations are included in the case where interfacial tension is calculated using equation (20), it is difficult to perform calculation on a single sheet, which results in calculation being complicated. However, in the case where equation (25) is used, since the calculation on a spreadsheet software is simplified, it is possible to control surface tension more easily.

In order to manufacture high strength coke using interfacial tension, there is a problem regarding what value the interfacial tension of a coal blend, which is determined by the blending ratios of the constituent kinds of coal, should be taken and controlled. Theoretically, it is preferable to minimize the interfacial tension in order to increase adhesive strength and coke strength. However, it is considered that there is a case where desired coke strength can be achieved in practical operation even if interfacial tension is not minimized. Therefore, a method described below is a suitable method for manufacturing high strength coke using interfacial tension, because the method provides wide variation of blending composition. That is, in the method, blending conditions are determined so that the interfacial tension of a coal blend is within a range in which desired coke strength can be achieved, using the relationship between interfacial tension and coke strength which is derived in advance by conducting coke strength tests using plural coal blends having various interfacial tensions.

In the case where high strength coke is manufactured by controlling interfacial tension, it is preferable that the control of a mean maximum reflectance of vitrinite (Ro) and a Gieseler maximum fluidity (log MF), which are conventional parameters for coal properties, be also used. This is because coke strength prediction using these conventional parameters for coal properties is effective to some extent and because the method for increasing coke strength according to the present invention is based on the principle different from that of these conventional parameters for coal properties. In practical operation, blending conditions are determined by the control so that the average value of a mean maximum reflectance of vitrinite (Ro) weighted by a blending ratio is 0.90 to 1.30 and the average value of a Gieseler maximum fluidity (log MF) weighted by a blending ratio is 2.3 to 2.8. In these controlling ranges, by further controlling interfacial tension, it is possible to increase the precision of coke strength prediction and to manufacture coke having higher strength.

The present inventors found that, in the case where interfacial tension $\gamma_{inter}$ which is derived using equation (20) is increased while the average value of the mean maximum reflectance of vitrinite (Ro) of a coal blend and the average value of the Gieseler maximum fluidity (log MF) of a coal blend are maintained constant, coke strength decreases with an increase of $\gamma_{inter}$ in the case where $\gamma_{inter}$ is more than 0.03 mN/m. Therefore, in the case where the average value of the mean maximum reflectance of vitrinite (Ro) of a coal blend and the average value of the Gieseler maximum fluidity (log MF) of a coal blend are used as indices for blending, it can be said that it is preferable that $\Gamma_{inter}$ be maintained to be 0.03 mN/m or less.

In addition, the present inventors found that, in the range of practical operation described above, in the case where the blending ratio of coal having a low MF is high, specifically in the case where the blending ratio of coal having a log MF of 1.4 or less is 30 mass % or more, there is an increase in the influence of interfacial tension on coke strength. The reason for this will be described hereafter.

It is known that the adhesion between coal particles is influenced not only by interfacial tension but also by fluidity. In the case where the blending ratio of coal having a low MF is low, since coal particles flow and soften together with each other, adhesion is significantly influenced not only by interfacial tension but also by this fluidity. It is considered that, in the case where the blending ratio of coal having a low MF is high, even if one coal particle softens, if another coal particle has a low MF, the coal particle having a low MF does not soften. Therefore, there is a decrease in adhesive effect due to fluidity, which results in an increase in the ratio of contribution of interfacial tension to adhesion. This is considered to be the reason why there is an increase in the influence of interfacial tension on coke strength in the case where the blending ratio of coal having a low MF is high. Nowadays, since there is an increase in the amount of non- or slightly-caking coal having a low MF due to a significant rise in the price of hard coking coal, it happens more often than before that the blending ratio of coal having a log MF of 1.4 or less is 30 mass % or more. Therefore, in view of the demand-supply situation of coal nowadays, the present method is effective as a method for increasing the strength of coke under the condition that the blending ratio of non- or slightly-caking coal is high. There is a similar tendency in the case of a coal blend having a lower MF than usual.

Specifically, in the case where the weighted average value of the log MF of a coal blend is 2.0 or more and less than 2.3, it is preferable that $\gamma_{inter}$ be maintained to be 0.02 mN/m or less in order to suppress a decrease in coke strength.

When referring to "coal brand", classification by brand name which is used when the coal is sold at a coal mine may be used. However, since there are some cases where blended coal consisting of the kinds of coal from different origins or different coal seams is sold as a single coal brand, and since coal properties generally vary depending on origin or coal seam, it is preferable that the kinds of coal from different origins or different coal seams be classified into different kinds of coal in the present invention. In this case, "coal brand (coal kind)" according to the present invention shall have nothing to do with brand name, and the present invention may be applied to coal which is sold as one coal brand at a coal mine by treating the coal as a coal blend consisting of various kinds of coal, or two or more kinds of coal. Here, "a coal seam" refers to each of plural coal layers which are generally present in layers in geological strata at a certain location. In the case where the kinds of coal are produced from adjacent coal seams of adjacent areas and there is only practically negligible difference in properties between these kinds of coal, the kinds of coal may be evaluated as the same kinds of coal.

The present invention may be applied not only to the blending of ordinary coal but also to the blending of coal briquettes. In addition, the present invention may also be applied to the case where, for example, pitch, oil coke, coke breeze, dust, waste plastics, or biomass is added in a small amount as an additive in addition to two or more kinds of coal. Here, "added in a small amount" means that an additive is added in an amount of about 10 mass % at most with respect to the total amount of coal, ordinarily 5 mass % or less. Since an additive is added in a small amount, it is also possible to derive a control index for determining blending ratios of the kinds of coal only from the interfacial tensions among the kinds of coal regardless of whether or not an additive is present when the present invention is applied.

As described above, the interfacial tension of coal can be suitably used as an index for evaluating not only the adhesive strength among the kinds of coal but also coke strength. For example, it is possible to increase the adhesive strength among the kinds of coal and coke strength by deriving in advance the relationship between interfacial tension and coke strength and by blending coal so that the interfacial tension of a coal blend is within a range in which desired coke strength is achieved. In addition, it is possible to predict coke strength from the viewpoint which is different from that of conventional indices by introducing this interfacial tension as a new parameter into a coke strength prediction formula. Therefore, it is possible to manufacture high strength coke without a significant increase in cost by taking interfacial tension into consideration.

EXAMPLES

Example 1

An example case where high strength coke was manufactured on the basis of interfacial tension will be described. In order to clarify the conditions for manufacturing high strength coke without depending on conventional parameters of coal properties, an experiment was carried out under the condition that conventional parameters of coal properties were constant. Thirteen kinds of coal (the kinds of coal A through M) were prepared, and, first, tests for the properties of these kinds of coal were carried out in order to determine mean maximum reflectance of vitrinite (Ro), Gieseler maximum fluidity (log MF), and surface tension derived by a film flotation method, which are conventional parameters of coal properties. Mean maximum reflectance was determined in accordance with JIS M 8816 (mean maximum reflectance of vitrinite of coal), and Gieseler maximum fluidity was determined in accordance with JIS M 8801. The measurement of surface tension by a film floatation method was carried out using a sample which was prepared by pulverizing coal into powders having a diameter of 200 μm or less, by heating the powder up to a temperature of 500° C. at a heating rate of 3° C./min, by rapidly cooling the heat-treated coal with liquefied nitrogen, by pulverizing the cooled coal into powders having a diameter of 150 μm or less, and by drying the pulverized powder in a dried nitrogen flow at a temperature of 120° C. for a duration of 2 hours. As a liquid used to determine surface tension in a film flotation method, ethanol, which is inexpensive and easy to handle, was used. The average value of surface tension distribution was derived from the determined surface tension using equation (10), and this average value of surface tension distribution was used as an index of surface tension of coal (γ). Using the results of the test for properties of coal, 4 classes of blend (blends A through D) having different interfacial tensions were determined. In order to eliminate the influences of other parameters on coke strength, the blending ratios of coal A through coal M were controlled so that all the blends have the same weighted average value of the maximum reflectance of vitrinite (Ro) of a coal blend and the same weighted average value of the Gieseler maximum fluidity (log MF) of a coal blend, which were used as conventional parameters for coke strength prediction. The average value of Ro of a coal blend and the average value of log MF of a coal blend were controlled to be equal to the values used in practical operation. Interfacial tension ($\gamma_{inter}$) was derived using equation (20). The properties of the 13 kinds of coal are given in Table 2, the blending ratios of the coal are given in Table 3, and the properties of the blends are given in Table 4.

TABLE 3-continued

| | Blending Ratio [mass %] | | | |
|---|---|---|---|---|
| Coal Kind | Blend A | Blend B | Blend C | Blend D |
| Coal D | 8.5 | 0 | 0 | 0 |
| Coal E | 0 | 9 | 0 | 0 |
| Coal F | 17 | 0 | 0 | 0 |
| Coal G | 0 | 0 | 3 | 5 |
| Coal H | 0 | 5 | 20 | 20 |
| Coal I | 20 | 30 | 0 | 30 |
| Coal J | 0 | 0 | 23 | 0 |
| Coal K | 20 | 0 | 0 | 0 |
| Coal L | 0 | 30 | 0 | 0 |
| Coal M | 0 | 0 | 30 | 30 |

TABLE 4

| Blend Name | $\overline{Ro}$ [—] | logMF [logddpm] | $\gamma_{inter}$ [mN/m] |
|---|---|---|---|
| Blend A | 1.01 | 2.35 | 0.006 |
| Blend B | 1.01 | 2.36 | 0.024 |
| Blend C | 1.01 | 2.35 | 0.037 |
| Blend D | 1.01 | 2.35 | 0.059 |

$\overline{Ro}$: Mean Value of Ro

In order to verify the influence of interfacial tension on coke strength, coke was manufactured using a test coke oven and evaluated. 16 kg each of the 4 classes of coal blend given in Table 3 was charged in an electric furnace under the conditions that coal particle having a diameter of 3 mm or less constituted 100 mass %, the humidity was 8 mass % and the bulk density of coal charge was 750 kg/m³ and then carbonized in an electric furnace. After carbonization had been performed under the conditions that the heating wall temperature was 1100° C. and the duration was 6 hours, nitrogen cooling was performed and then a drum test was carried out. Using a drum test method according to JIS K 2151, the mass ratio of coke having a particle diameter of 15 mm or more was determined after 150 rotations had been performed at a rotation speed of 15 rpm, and then the ratio of the mass ratio with respect to that before the rotations× 100 was calculated and defined as drum index DI150/15.

Figure 5:
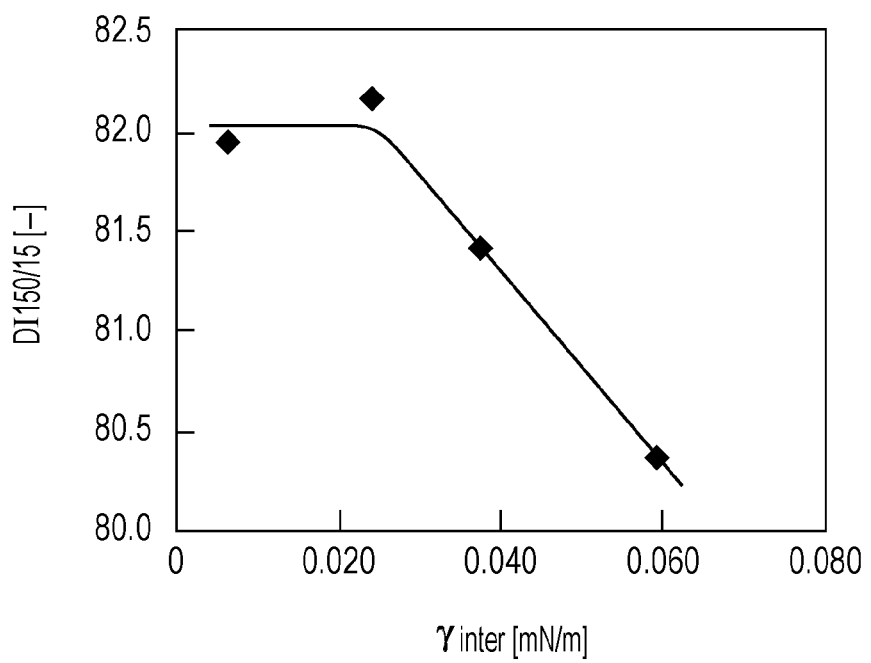
FIG. 5 is a graph illustrating the influence of interfacial tension on drum index of coke.

The relationship between the interfacial tension ($\gamma_{inter}$) and the drum index of coke is illustrated in FIG. 5. FIG. 5 indicates that there is a tendency for drum index of coke to increase with a decrease in interfacial tension. However, in the case where interfacial tension was 0.03 mN/m or less, coke strength was almost constant independently of interfacial tension. Since 4 classes of blend in this example had

TABLE 2

| Coal Kind | Ro [—] | logMF [logddpm] | γ [mN/m] | Ash [%, d.b.] | VM [%, d.b.] | C [%, d.a.f.] | H [%, d.a.f.] | N [%, d.a.f.] | S [%, d.a.f.] | O [%, d.a.f.] |
|---|---|---|---|---|---|---|---|---|---|---|
| Coal A | 1.29 | 1.04 | 40.6 | 7.3 | 20.8 | 89.0 | 4.58 | 1.88 | 0.43 | 4.13 |
| Coal B | 0.76 | 2.21 | 40.2 | 9.2 | 35.4 | 83.5 | 5.41 | 1.91 | 0.46 | 8.77 |
| Coal C | 0.68 | 4.11 | 41.1 | 5.4 | 42.4 | 84.4 | 6.01 | 2.04 | 1.00 | 6.59 |
| Coal D | 0.75 | 1.82 | 40.6 | 9.0 | 37.7 | 83.0 | 5.55 | 1.89 | 0.66 | 8.86 |
| Coal E | 0.99 | 1.15 | 40.9 | 9.8 | 25.4 | 86.7 | 4.96 | 2.02 | 0.50 | 5.78 |
| Coal F | 0.98 | 2.88 | 40.2 | 8.8 | 26.9 | 87.4 | 5.03 | 1.79 | 0.43 | 5.35 |
| Coal G | 0.82 | 4.43 | 39.9 | 8.4 | 35.5 | 85.2 | 5.71 | 3.01 | 0.51 | 5.60 |
| Coal H | 0.98 | 3.08 | 39.6 | 7.9 | 28.2 | 86.5 | 5.16 | 2.07 | 0.47 | 5.78 |
| Coal I | 0.85 | 3.13 | 40.9 | 8.8 | 34.5 | 84.5 | 5.40 | 2.23 | 0.61 | 7.26 |
| Coal J | 0.89 | 3.59 | 39.1 | 7.1 | 33.7 | 84.8 | 5.60 | 2.27 | 0.61 | 6.71 |
| Coal K | 1.07 | 3.18 | 39.7 | 9.2 | 27.0 | 87.5 | 5.13 | 1.35 | 0.29 | 5.72 |
| Coal L | 1.10 | 2.03 | 38.9 | 8.7 | 25.5 | 87.4 | 5.04 | 1.47 | 0.59 | 5.52 |
| Coal M | 1.15 | 1.49 | 37.6 | 10.0 | 23.3 | 88.0 | 4.79 | 1.30 | 0.45 | 5.50 |

$\overline{Ro}$: Mean Value of Ro

TABLE 3

| | Blending Ratio [mass %] | | | |
|---|---|---|---|---|
| Coal Kind | Blend A | Blend B | Blend C | Blend D |
| Coal A | 28 | 18 | 12 | 12 |
| Coal B | 0 | 8 | 12 | 3 |
| Coal C | 6.5 | 0 | 0 | 0 | almost the same values of the conventional parameters (the weighted average value of Ro of a coal blend and the weighted value of log MF of a coal blend) which were used to predict coke strength, it can be said that this result could not have been presumed from conventional knowledge. In addition, coke strength after $CO_2$ reaction (determined using a method according to ISO 18894) was, for example, 64.5 for blend B and 63.4 for blend C, which means that there was a decrease in strength in the case where interfacial tension was more than 0.03 mN/m. Therefore, it is clarified that it is at least necessary to control interfacial tension to be 0.03 mN/m or less in order to sufficiently increase coke strength in consideration of interfacial tension. That is to say, in the case where coke is manufactured by blending plural kinds of coal, it is clarified that it is possible to manufacture coke having higher strength than before by blending the kinds of coal so that interfacial tension is decreased at least down to 0.03 mN/m or less in addition to controlling the conventional parameters of coal properties. From the results described above, it is clarified that it is possible to manufacture coke having higher strength than before by determining blending conditions using the method according to the present invention.

Example 2

An example case where high strength coke was manufactured by controlling interfacial tension under the condition that the blending ratio of coal having a low MF is high. Eight kinds of coal were prepared, and, first, tests for coal properties using these kinds of coal were carried out. The measurement items were Ro (mean maximum reflectance), log MF, and surface tension as is the case with [EXAMPLE 1] described above. The measurement methods were also the same as those in [EXAMPLE 1]. The average value of surface tension distribution was derived from the determined surface tension distribution using equation (10), and this average value of surface tension distribution was used as an index of surface tension (γ). Using the results of the tests for coal properties, 5 classes of blend (blends E through I) having different interfacial tensions were determined. In order to eliminate the influences of other parameters on coke strength, the blending ratios of all the kinds of coal were controlled so that all the blends have the same weighted average value of the maximum reflectance of vitrinite (Ro) of a coal blend and the same weighted average value of the Gieseler maximum fluidity (log MF) of a coal blend, which are used as conventional parameters for coke strength prediction. In addition, the blends were determined so that the blending ratio of coal having a log MF of 1.4 or less was 30 mass % or more. The weighted average of the mean value of Ro of a coal blend and the weighted average of log MF of a coal blend were controlled to be equal to the values used in practical operation. As interfacial tension, $\gamma_{inter}$ defined by equation (20) was used. The properties of the 8 kinds of coal are given in Table 5, the blending ratios of the kinds of coal are given in Table 6, and the properties of coal blends are given in Table 7.

TABLE 5

| Coal Kind | Ro [—] | logMF [logddpm] | γ [mN/m] | Ash [%, d.b.] | VM [%, d.b.] | C [%, d.a.f.] | H [%, d.a.f.] | N [%, d.a.f.] | S [%, d.a.f.] | O [%, d.a.f.] |
|---|---|---|---|---|---|---|---|---|---|---|
| Coal A | 1.29 | 1.04 | 40.6 | 7.27 | 20.76 | 88.98 | 4.58 | 1.88 | 0.43 | 4.13 |
| Coal C | 0.68 | 4.11 | 41.1 | 5.40 | 42.40 | 84.36 | 6.01 | 2.04 | 1.00 | 6.59 |
| Coal D | 0.75 | 1.82 | 40.6 | 9.00 | 37.70 | 83.04 | 5.55 | 1.89 | 0.66 | 8.86 |
| Coal F | 0.98 | 2.88 | 40.2 | 8.80 | 26.90 | 87.39 | 5.03 | 1.79 | 0.43 | 5.35 |
| Coal I | 0.85 | 3.13 | 40.9 | 8.80 | 34.50 | 84.50 | 5.40 | 2.23 | 0.61 | 7.26 |
| Coal J | 0.89 | 3.59 | 39.1 | 7.05 | 33.70 | 84.81 | 5.60 | 2.27 | 0.61 | 6.71 |
| Coal N | 1.10 | 3.69 | 40.6 | 8.80 | 27.70 | 87.58 | 5.24 | 2.24 | 0.79 | 4.15 |
| Coal O | 1.06 | 3.21 | 38.9 | 8.50 | 25.05 | 87.39 | 5.20 | 1.90 | 0.55 | 4.97 |

R̄o: Mean Value of Ro

TABLE 6

| | Blending Ratio [mass %] | | | | |
|---|---|---|---|---|---|
| Coal Kind | Blend E | Blend F | Blend G | Blend H | Blend I |
| Coal A | 30 | 30 | 30 | 30 | 35 |
| Coal C | 16 | 5 | 4 | 13 | 12 |
| Coal D | 22 | 4 | 10 | 20 | 4 |
| Coal F | 2 | 31 | 26 | 7 | 24 |
| Coal I | 0 | 30 | 0 | 0 | 25 |
| Coal J | 0 | 0 | 30 | 0 | 0 |
| Coal N | 30 | 0 | 0 | 0 | 0 |
| Coal O | 0 | 0 | 0 | 30 | 0 |

TABLE 7

| Blend Name | R̄o [—] | logMF [logddpm] | Blending Ratio of Coal Having logMF of 1.4 or Less [mass %] | $\gamma_{inter}$ [mN/m] |
|---|---|---|---|---|
| Blend E | 1.01 | 2.34 | 30 | 0.001 |
| Blend F | 1.01 | 2.36 | 30 | 0.003 |
| Blend G | 1.01 | 2.35 | 30 | 0.014 |
| Blend H | 1.01 | 2.34 | 30 | 0.022 |
| Blend I | 1.01 | 2.35 | 35 | 0.003 |

R̄o: Mean Value of Ro

In order to verify the influence of interfacial tension on coke strength, a carbonizing test and a drum test were carried out as done in [EXAMPLE 1]. The relationship between interfacial tension ($\gamma_{inter}$) and drum index of coke is illustrated in FIG. 6.

Figure 6:
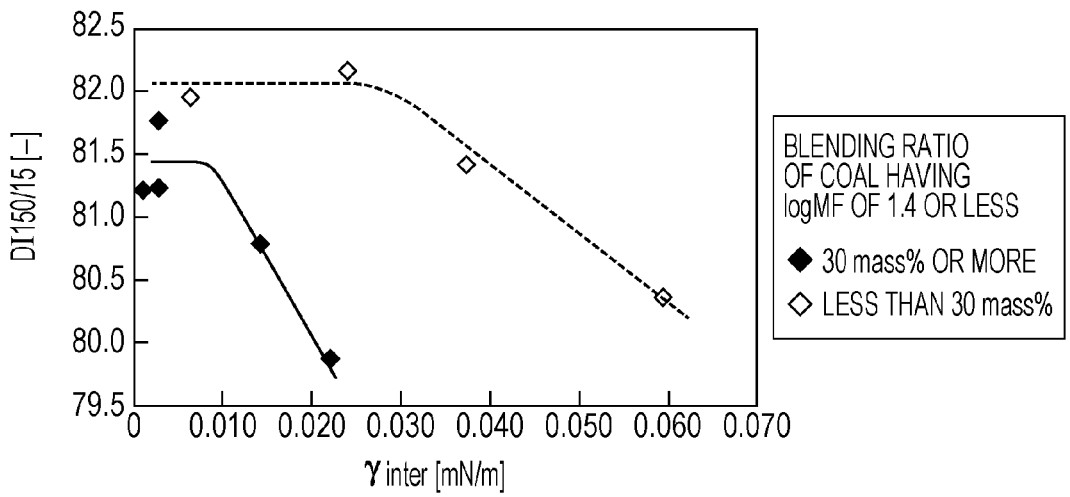
FIG. 6 is a graph illustrating the influence of interfacial tension on the drum index of coke derived from coal blends containing large amount of low MF coals.

FIG. 6 indicates that, even in the case where the blending ratio of coal having low MF is 30 mass % or more, there is a tendency for drum index of coke to increase with a decrease in interfacial tension as is the case with [EXAMPLE 1]. For reference, the results of [EXAMPLE 1] are also illustrated in FIG. 6 as an example case where the blending ratio of coal having a log MF of 1.4 or less is less than 30 mass %. Coke strength after $CO_2$ reaction (determined using a method according to ISO 18894) also has the same tendency as drum index of coke, and the coke strength after $CO_2$ reaction was, for example, 63.6 for blend 1 and 62.5 for blend G, which means that strength decreases with an increase in interfacial tension. In comparison of the results of [EXAMPLE 1] with those of [EXAMPLE 2], which are the results in the case where the blending ratio of coal having a log MF of 1.4 or less is 30 mass % or more, the range of interfacial tension in which strength is not decreased was narrowed from 0.03 mN/m to 0.01 mN/m by increasing the blending ratio of coal having a log MF of 1.4 or less. Therefore, in the case where the blending ratio of coal having low MF, specifically in the case where the blending ratio of coal having a log MF of 1.4 or less is 30 mass % or more, it is clarified that it is possible to manufacture coke having higher strength than before by blending coal so that the interfacial tension is small, at least down to 0.01 mN/m or less, in addition to optimizing conventional parameters of coke properties. From the results described above, it is clarified that it is possible to manufacture coke having higher strength than before by determining blending conditions using the method according to the present invention.

Example 3

An example case where high strength coke was manufactured by controlling interfacial tension which is predicted from the variance of the surface tensions of all the kinds of coal constituting a coal blend. The same measurement items and the same results of the tests as used in [EXAMPLE 1] and [EXAMPLE 2] are used with the exception that interfacial tension is derived from equation (25). The calculation results of the interfacial tensions of blends A through I using equation (25) are given in Table 8.

TABLE 8

| Blend Name | $\gamma_{inter}$ by Equation (25) | $\gamma_{inter}$ by Equation (20) |
| --- | --- | --- |
| Blend A | 0.006 | 0.006 |
| Blend B | 0.024 | 0.024 |
| Blend C | 0.037 | 0.037 |
| Blend D | 0.059 | 0.059 |
| Blend E | 0.001 | 0.001 |
| Blend F | 0.003 | 0.003 |
| Blend G | 0.014 | 0.014 |
| Blend H | 0.022 | 0.022 |
| Blend I | 0.003 | 0.003 |

For reference, $\gamma_{inter}$ which was derived using equation (20) is also given in Table 8. As indicated by Table 8, it is confirmed that the value of $\gamma_{inter}$ derived from equation (20) and that derived from equation (25) are almost the same. Therefore, it is considered that the relationship between interfacial tension and drum index of coke, where interfacial tension derived from equation (25) is used, is also almost the same as that in [EXAMPLE 1] or [EXAMPLE 2]. From the results described above, it is clarified that it is possible to manufacture coke having higher strength than before by determining blending conditions by predicting interfacial tension by equation (25).

Example 4

Using 18 kinds of coal which were different in terms of brand name or lot from those used in EXAMPLES 1 through 3, the influence of the interfacial tension of a coal blend on coke strength was investigated under the condition that the fluidity of a coal is low. The properties of the kinds of coal used are given in Table 9.

TABLE 9

| Coal Name | Ro [—] | MF [logddpm] | γ [mN/m] | Ash [%, d. b.] | VM [%, d. b.] |
| --- | --- | --- | --- | --- | --- |
| Coal P | 0.73 | 2.74 | 41.4 | 9.1 | 34.2 |
| Coal Q | 0.75 | 2.73 | 40.7 | 5.2 | 39.9 |
| Coal R | 0.76 | 3.42 | 42.1 | 9.8 | 36.2 |
| Coal S | 0.83 | 3.91 | 41.3 | 9.6 | 33.7 |
| Coal T | 0.90 | 3.82 | 41.9 | 8.0 | 33.4 |
| Coal U | 0.98 | 2.88 | 40.1 | 8.9 | 26.8 |
| Coal V | 0.99 | 1.15 | 40.9 | 9.6 | 25.8 |
| Coal W | 1.00 | 2.60 | 41.5 | 8.9 | 26.8 |
| Coal X | 1.05 | 2.97 | 40.2 | 9.2 | 27.4 |
| Coal Y | 1.08 | 1.85 | 40.7 | 8.9 | 23.5 |
| Coal Z | 1.16 | 2.70 | 39.4 | 10.4 | 22.5 |
| Coal a | 1.16 | 1.98 | 40.1 | 9.6 | 22.9 |
| Coal b | 1.29 | 1.04 | 40.6 | 7.5 | 19.8 |
| Coal c | 1.45 | 1.76 | 39.5 | 9.2 | 18.8 |
| Coal d | 1.46 | 1.72 | 39.9 | 10.0 | 19.1 |
| Coal e | 1.53 | 0.00 | 37.8 | 8.3 | 17.2 |
| Coal f | 1.55 | 0.70 | 40.6 | 12.3 | 18.1 |
| Coal g | 1.62 | 0.70 | 37.7 | 9.5 | 18.8 |

Using the results of the tests for coal properties given in Table 9, 6 classes in total of blends were determined so that the blends have an average log MF of a coal blend of 2.00, 2.30, or 2.50, while the three classes have an interfacial tension of 0.01 to 0.02 mN/m or 0.04 to 0.05 mN/m. In addition, $\gamma_{inter}$ which was defined by equation (1) was used as interfacial tension. In order to eliminate the influences of other parameters on coke strength, the blending ratios of coal P through coal g were controlled so that all the blends have the same average value of the maximum reflectance of vitrinite (Ro) of a coal blend which is used as a conventional parameter for coke strength prediction. The weighted average value of Ro or log MF of a coal blend is derived from an equation such as equation (26) which is an example in the case of log MF.

[Math. 14]

$$m_c = \sum_{i=1}^{n} m_i w_i \qquad (26)$$

Here, $m_i$: the log MF (the logarithm of Gieseler maximum fluidity) of coal i, $w_i$: the blending ratio of coal i, and $m_c$: the log MF (the logarithm of maximum fluidity) of a coal blend, while equation (17) is satisfied. The blending ratios of the kinds of coal and the properties of the coal blends are given in Table 10.

TABLE 10

| Coal Name | Blending Ratio | | | | | |
| --- | --- | --- | --- | --- | --- | --- |
| | $\gamma_{inter}$: 0.01-0.02 Nm/m | | | $\gamma_{inter}$: 0.04-0.05 Nm/m | | |
| Coal P | 0 | 15 | 15 | 22 | 21 | 5 |
| Coal Q | 27 | 0 | 0 | 0 | 0 | 0 |
| Coal R | 0 | 0 | 6 | 0 | 0 | 0 |
| Coal S | 0 | 0 | 8 | 0 | 13 | 0 |
| Coal T | 0 | 10 | 0 | 15 | 0 | 35 |
| Coal U | 0 | 28 | 0 | 0 | 0 | 0 |
| Coal V | 14 | 0 | 0 | 15 | 0 | 19 |
| Coal W | 0 | 0 | 19 | 16 | 13 | 0 |
| Coal X | 28 | 0 | 20 | 0 | 25 | 0 |
| Coal Y | 0 | 23 | 6 | 0 | 0 | 0 |
| Coal Z | 0 | 0 | 0 | 0 | 0 | 11 |
| Coal a | 0 | 0 | 0 | 0 | 0 | 21 |
| Coal b | 25 | 13 | 11 | 19 | 13 | 0 |
| Coal c | 0 | 6 | 0 | 0 | 0 | 3 |
| Coal d | 0 | 0 | 15 | 0 | 0 | 0 |
| Coal e | 6 | 0 | 0 | 7 | 15 | 0 |
| Coal f | 0 | 5 | 0 | 0 | 0 | 0 |

TABLE 10-continued

| Coal | Blending Ratio | | | | | |
|---|---|---|---|---|---|---|
| Name | $\gamma_{inter}$: 0.01-0.02 Nm/m | | | $\gamma_{inter}$: 0.04-0.05 Nm/m | | |
| Coal g | 0 | 0 | 0 | 6 | 0 | 6 |
| Ro of Coal Blend | 1.05 | 1.05 | 1.05 | 1.05 | 1.05 | 1.05 |
| logMF of Coal Blend | 2.00 | 2.30 | 2.50 | 2.00 | 2.30 | 2.50 |
| $\gamma_{inter}$ of Coal Blend | 0.02 | 0.01 | 0.01 | 0.05 | 0.05 | 0.04 |

Figure 7:
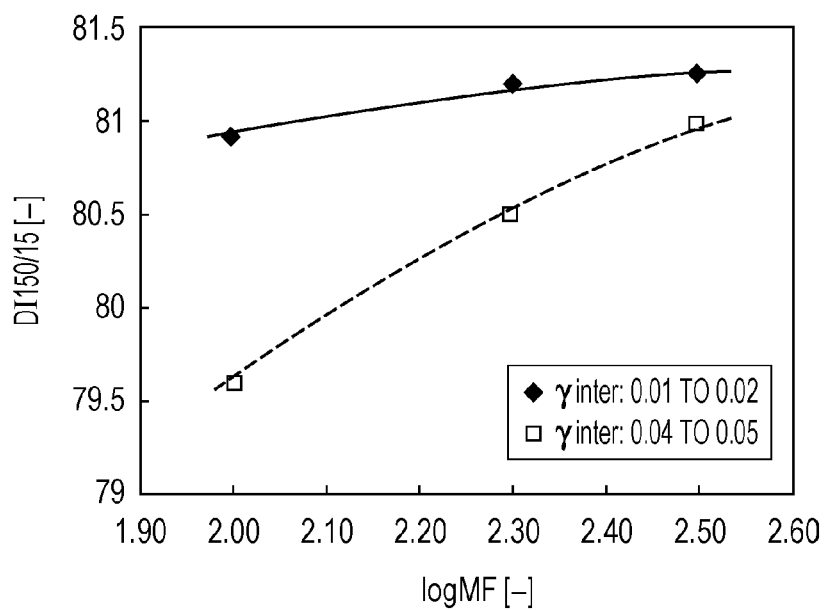
FIG. 7 is a diagram illustrating the relationship between the drum index of the coke produced in EXAMPLE 4 and the log MF of coal blends.

Coke was manufactured and evaluated as done in EXAMPLES described above. A drum test was carried out using the 6 classes of coal blends given in Table 10. The relationship between MF and drum index of coke is illustrated in FIG. 7. FIG. 7 indicates that, while coke strength did not decrease even for log(MF/[ddpm])=2.0 in comparison to that for log(MF/[ddpm])=2.5 in the case of the classes having an interfacial tension of 0.01 to 0.02 mN/m, coke strength decreased for log(MF/[ddpm])=2.0 in the case of the classes having an interfacial tension of 0.04 to 0.05 mN/m. From this result, it is clarified that a point (critical fluidity point), at which coke strength begins decreasing due to a decrease in fluidity, is decreased down to the point of log(MF/[ddpm])=2.0 by controlling interfacial tension to be 0.01 to 0.02 mN/m. Therefore, it is clarified that, even in the case of a blend having a log(MF/[ddpm]) of 2.0 where sufficient coke strength could not be achieved using conventional blend, it is possible to suppress a decrease in strength by controlling the interfacial tension of a coal blend to be 0.02 mN/m or less. In this case also, there was the similar tendency in coke strength after $CO_2$ reaction (determined using a method according to ISO 18894), and it was possible to suppress a decrease in strength even in the case of a blend having a log(MF/[ddpm]) of 2.0 by controlling interfacial tension to be 0.02 mN/m or less. From the results described above, it is possible to manufacture high strength coke by determining the blending conditions using the method according the present invention, even in the case where critical fluidity is decreased to the level lower than before and the MF is decreased down to a level at which high strength coke could not be manufactured by conventional methods.

Example 5

Coke was manufactured and the strength of the coke was evaluated as done in EXAMPLES 1 through 4 described above by preparing coal blends having various weighted average values of Ro, weighted average values of log MF, and interfacial tension and consisting of plural kinds of coal. Here, interfacial tension of a coal blend was calculated using equation (2). The properties of coal blends and the measurement results of the strength of the obtained coke are given in Table 11.

TABLE 11

| Ro (%) | logMF (logddpm) | $\gamma_{inter}$ (mN/m) | DI150/15 (—) | |
|---|---|---|---|---|
| 0.90 | 2.30 | 0.027 | 81.6 | Example |
| 0.90 | 2.30 | 0.032 | 81.1 | Comparative Example |
| 0.90 | 2.80 | 0.025 | 81.8 | Example |
| 0.90 | 2.80 | 0.035 | 81.0 | Comparative Example |

TABLE 11-continued

| Ro (%) | logMF (logddpm) | $\gamma_{inter}$ (mN/m) | DI150/15 (—) | |
|---|---|---|---|---|
| 1.30 | 2.30 | 0.022 | 84.2 | Example |
| 1.30 | 2.30 | 0.032 | 83.8 | Comparative Example |
| 1.30 | 2.80 | 0.030 | 84.5 | Example |
| 1.30 | 2.80 | 0.036 | 83.9 | Comparative Example |

From these results, for a wide range of the composition of coal blends, it is confirmed that, in the case where interfacial tension $\gamma_{inter}$ of a coal blend is more than 0.03, there is a decrease in coke strength, and thus it is preferable that interfacial tension of a coal blend be 0.03 mN/m or less.

Example 6

By preparing the sample of heat treated coal by the same method as used in EXAMPLE 1 at various temperatures and by determining the surface tension of the coal, it was confirmed that there is a tendency for surface tension to increase with an increase in heat treatment temperature in a temperature range equal to and higher than the temperature at which softening occurs. For example, as Table 12 indicates, in the case where the heat treatment temperature was 400° C., 450° C., 500° C., 600° C., and 800° C., the values of the surface tension of coal C were respectively 33.0, 35.5, 41.1, 45.2, and 52.3 mN/m, and the values of the surface tension of coal M were respectively 30.4, 32.4, 37.6, 42.2, and 48.7 mN/m. The surface tensions of other kinds of coal given in Table 2 were almost between the values for coal C and coal M at all the temperatures described above.

TABLE 12

| | Heat Treatment Temperature (° C.) | | | | |
|---|---|---|---|---|---|
| | 400 | 450 | 500 | 600 | 800 |
| Surface Tension of Coal C mN/m | 33.0 | 35.5 | 41.1 | 45.2 | 52.3 |
| Surface Tension of Coal M mN/m | 30.4 | 32.4 | 37.6 | 42.2 | 48.7 |

As described above, it was confirmed that there is a tendency for the surface tension of heat treated coal to monotonically increase with an increase in heat treatment temperature, and that, in particular at a temperature equal to or higher than 450° C., there is a tendency for the surface tensions of all the evaluated kinds of coal to monotonically increase with an increase in heat treatment temperature (tendency near to linear correlation with temperature). By utilizing this tendency, from the correlation between surface tension and heat treatment temperature obtained using samples of certain coal which are prepared at two or more heat treatment temperatures, it is possible to precisely predict surface tension at any temperature within the range of the heat treatment temperatures. Therefore, the surface tension of certain coal may be predicted in this way. From the calculation results of the value of interfacial tension $\gamma_{inter}$ of coal blends for various heat treatment temperatures, as Table 13 indicates, the $\gamma_{inter}$ of coal blend B which is derived from equation (20) using surface tensions of the constituent heat treated kinds of coal which was treated at a temperature of 400° C. was 0.023 mN/m, and the values of interfacial tension $\gamma_{inter}$ for temperatures of 450° C., 600° C., and 800° C. were respectively 0.023 mN/m, 0.025 mN/m, and 0.26 mN/m, which means that there is not a large difference among interfacial tensions for different heat treatment temperatures. Also, in the case of coal blend C, the interfacial tensions of the coal blend derived from surface tensions of constituent heat treated kinds of coal which were treated at temperatures of 400° C., 450° C., 600° C., and 800° C. were respectively 0.034 mN/m, 0.036 mN/m, 0.039 mN/m, and 0.039 mN/m, which means that there is not a large difference among interfacial tensions for different heat treatment temperatures. That is to say, it is clarified that it is possible to manufacture high strength coke, even in the case where a heat treatment temperature is changed, by blending coal so that the interfacial tension is 0.03 mN/m or less. Here, since the surface tension of heat treated coal is influenced by heat treatment temperature, it is necessary to calculate the interfacial tension of a coal blend using the values of surface tension of all the constituent kinds of coal which are derived from the samples which are treated at the same heat treatment temperature or predicted for the same heat treatment temperature.

TABLE 13

| | Heat Treatment Temperature (° C.) | | | |
|---|---|---|---|---|
| | 400 | 450 | 600 | 800 |
| $\gamma_{inter}$ of Coal Blend B mN/m | 0.023 | 0.023 | 0.025 | 0.026 |
| $\gamma_{inter}$ of Coal Blend C mN/m | 0.034 | 0.036 | 0.039 | 0.039 |

REFERENCE SIGNS LIST 1 gaseous phase
2 liquid
3 sample particle
4 surface tension
5 peak value of surface tension distribution
6 minimum surface tension of surface tension distribution
7 maximum surface tension of surface tension distribution
8 coal A
9 coal B
10 (10a, 10b, 10c, 10d) contact interface between coal particles
11 schematic diagram of cross section inside coke derived from coal blend consisting of coal A and coal B

The invention claimed is:

1. A method for manufacturing coke from a blend of two or more types of coals, the method comprising:
   deriving a mathematical relationship between an interfacial tension of a coal blend consisting of two or more kinds of coal and a strength of coke which is manufactured by carbonizing the coal blend, wherein the interfacial tension of the coal blend is determined by measuring the surface tension of the two or more kinds of coal in the blend then using a mathematical relationship between the surface tension of the kinds of coal and the interfacial tension of the coal blend to determine the interfacial tension;
   determining an optimal blending ratio for the two or more kinds of coal using the mathematical relationship between the interfacial tension of the coal blend and the strength of coke which is manufactured by carbonizing the coal blend;
   blending the two or more kinds of coal according to the optimal blending ratio to create an optimal coal blend, wherein the optimal coal blend will be converted to a coke when carbonized; and
   carbonizing the optimal coal blend to form the coke,
   wherein the surface tension of the coal is a surface tension obtained by heating the coal at a temperature of 350° C. or higher and 800° C. or lower, by cooling the heated coal under an inert gas atmosphere, and by performing measurement using the cooled coal.

2. The method for manufacturing coke according to claim 1, wherein the interfacial tension among the kinds of coal is an interfacial tension $\gamma_{inter}$ derived from equation (1) below using the surface tension of each kind of coal:

$$\gamma_{inter} = W\Gamma W^t, \quad (1)$$

where $$\Gamma = \begin{pmatrix} \gamma_{11} & \gamma_{12} & \cdots & \gamma_{1j} & \cdots & \gamma_{1n} \\ \gamma_{21} & \gamma_{22} & & & & \vdots \\ \vdots & & \ddots & & & \vdots \\ \gamma_{i1} & & & \gamma_{ij} & & \gamma_{in} \\ \vdots & & & & \ddots & \vdots \\ \gamma_{n1} & \cdots & \cdots & \gamma_{nj} & \cdots & \gamma_{nn} \end{pmatrix}$$

$$\gamma_{ij} = \gamma_i + \gamma_j - 2\exp[-\beta(\gamma_i - \gamma_j)^2]\sqrt{\gamma_i \gamma_j}$$

$$\gamma_{ij} = \gamma_{ji}$$

$$W = (w_1 \quad w_2 \quad \ldots \quad w_i \quad \ldots \quad w_n)$$

$$\sum_{i=1}^{n} w_i = 1$$

$\gamma_i$: the surface tension of coal i
$\gamma_{ij}$: the interfacial tension between coal i and coal j
$w_i$: the blending ratio of coal i
$\gamma_{inter}$: the interfacial tension of a coal blend consisting of coal 1, coal 2, . . . , coal i, . . . and coal n.

3. The method for manufacturing coke according to claim 2, wherein the blending ratio of each kind of coal is determined so that the interfacial tension $\gamma_{inter}$ is 0.03 mN/m or less.

4. The method for manufacturing coke according to claim 2, wherein a coal blend having a weighted average value of Ro of the constituent kinds of coal of 0.90% or more and 1.30% or less and a weighted average value of logMF of the constituent kinds of coal of 2.3 or more and 2.8 or less is used, where Ro is a mean maximum reflectance and MF is a Gieseler maximum fluidity.

5. The method for manufacturing coke according to claim 2, wherein the blending ratio of each kind of coal is determined so that the interfacial tension $\gamma_{inter}$ is 0.02 mN/m or less in the case of a coal blend having a weighted average value of Ro of the constituent kinds of coal of 0.90% or more and 1.30% or less and a weighted average value of logMF of the constituent kinds of coal of 2.0 or more and less than 2.3, where Ro is a mean maximum reflectance and MF is a Gieseler maximum fluidity.

6. The method for manufacturing coke according to claim 2, wherein the blending ratio of each kind of coal is determined so that the interfacial tension $\gamma_{inter}$ is 0.01 mN/m or less in the case of a coal blend containing 30 mass % or more of coal having a logMF of 1.4 or less, where MF is a Gieseler maximum fluidity.

7. The method for manufacturing coke according to claim 1, wherein the interfacial tension among the kinds of coal is an interfacial tension $\gamma_{inter}$ derived from equation (2) below using the surface tension of each kind of coal:

$$\gamma_{inter} = 0.032\sigma_\gamma^2, \quad (2)$$

where $$\sigma_\gamma^2 = \frac{100}{100\sum_{i=1}^{n} w_i - 1} \left[ \sum_{i=1}^{n} \gamma_i^2 w_i - \frac{\left(\sum_{i=1}^{n} \gamma_i w_i\right)^2}{\sum_{i=1}^{n} w_i} \right]$$

$$\sum_{i=1}^{n} w_i = 1$$

$\gamma_i$: the surface tension of coal i
$w_i$: the blending ratio of coal i
$\gamma_{inter}$: the interfacial tension of a coal blend consisting of coal 1, coal 2, ..., coal i, ... and coal n
$\sigma_\gamma^2$: the variance of the surface tensions of all the constituent kinds of coal.

8. The method for manufacturing coke according to claim 7, wherein the blending ratio of each kind of coal is determined so that the interfacial tension $\gamma_{inter}$ is 0.03 mN/m or less.

9. The method for manufacturing coke according to claim 7, wherein a coal blend having a weighted average value of Ro of the constituent kinds of coal of 0.90% or more and 1.30% or less and a weighted average value of logMF of the constituent kinds of coal of 2.3 or more and 2.8 or less is used, where Ro is a mean maximum reflectance and MF is a Gieseler maximum fluidity.

10. The method for manufacturing coke according to claim 7, wherein the blending ratio of each kind of coal is determined so that the interfacial tension $\gamma_{inter}$ is 0.02 mN/m or less in the case of a coal blend having a weighted average value of Ro of the constituent kinds of coal of 0.90% or more and 1.30% or less and a weighted average value of logMF of the constituent kinds of coal of 2.0 or more and less than 2.3, where Ro is a mean maximum reflectance and MF is a Gieseler maximum fluidity.

11. The method for manufacturing coke according to claim 7, wherein the blending ratio of each kind of coal is determined so that the interfacial tension $\gamma_{inter}$ is 0.01 mN/m or less in the case of a coal blend containing 30 mass % or more of coal having a logMF of 1.4 or less, where MF is a Gieseler maximum fluidity.

12. A method for manufacturing coke from a blend of two or more types of coals, the method comprising:
deriving a mathematical relationship between an interfacial tension of a coal blend consisting of two or more kinds of coal and a strength of coke which is manufactured b carbonizing the coal blend, wherein the interfacial tension of the coal blend is determined by measuring the surface tension of the two or more kinds of coal in the blend then using a mathematical relationship between the surface tension of the kinds of coal and the interfacial tension of the coal blend to determine the interfacial tension;
determining an optimal blending ratio for the two or more kinds of coal using the mathematical relationship between the interfacial tension of the coal blend and the strength of coke which is manufactured by carbonizing the coal blend;
blending the two or more kinds of coal according to the optimal blending ratio to create an optimal coal blend, wherein the optimal coal blend will be converted to a coke when carbonized; and
carbonizing the optimal coal blend to form the coke, wherein the surface tension of the coal is a surface tension obtained by heating the coal at a temperature of an initial softening temperature or more and a solidification temperature or less, by cooling the heated coal under an inert gas atmosphere, and by performing measurement using the cooled coal.

13. The method for manufacturing coke according to claim 12, wherein the interfacial tension among the kinds of coal is an interfacial tension $\gamma_{inter}$ derived from equation (1) below using the surface tension of each kind of coal:

$$\gamma_{inter} = W\Gamma W^t, \text{ where} \quad (1)$$

$$\Gamma = \begin{bmatrix} \gamma_{11} & \gamma_{12} & \cdots & \gamma_{1j} & \cdots & \gamma_{1n} \\ \gamma_{21} & \gamma_{22} & & & & \vdots \\ \vdots & & \ddots & & & \vdots \\ \gamma_{i1} & & & \gamma_{ij} & & \gamma_{in} \\ \vdots & & & & \ddots & \vdots \\ \gamma_{n1} & \cdots & \cdots & \gamma_{nj} & \cdots & \gamma_{nn} \end{bmatrix}$$

$$\gamma_{ij} = \gamma_i + \gamma_j - 2\exp[-\beta(\gamma_i - \gamma_j)^2]\sqrt{\gamma_i\gamma_j}$$

$$\gamma_{ij} = \gamma_{ji}$$

$$W = (w_1 \; w_2 \; \ldots \; w_i \; \ldots \; w_n)$$

$$\sum_{i=1}^{n} w_i = 1$$

$\gamma_i$: the surface tension of coal i
$\gamma_{ij}$: the interfacial tension between coal i and coal j
$w_i$: the blending ratio of coal i
$\gamma_{inter}$: the interfacial tension of a coal blend consisting of coal 1, coal 2, ..., coal i, ... and coal n.

14. The method for manufacturing coke according to claim 13, wherein the blending ratio of each kind of coal is determined so that the interfacial tension $\gamma_{inter}$ is 0.03 mN/m or less.

15. The method for manufacturing coke according to claim 13, wherein a coal blend having a weighted average value of Ro of the constituent kinds of coal of 0.90% or more and 1.30% or less and a weighted average value of logMF of the constituent kinds of coal of 2.3 or more and 2.8 or less is used, where Ro is a mean maximum reflectance and MF is a Gieseler maximum fluidity.

16. The method for manufacturing coke according to claim 13, wherein the blending ratio of each kind of coal is determined so that the interfacial tension $\gamma_{inter}$ is 0.02 mN/m or less in the case of a coal blend having a weighted average value of Ro of the constituent kinds of coal of 0.90% or more and 1.30% or less and a weighted average value of logMF of the constituent kinds of coal of 2.0 or more and less than 2.3, where Ro is a mean maximum reflectance and MF is a Gieseler maximum fluidity.

17. The method for manufacturing coke according to claim 13, wherein the blending ratio of each kind of coal is determined so that the interfacial tension $\gamma_{inter}$ is 0.01 mN/m or less in the case of a coal blend containing 30 mass % or more of coal having a logMF of 1.4 or less, where MF is a Gieseler maximum fluidity.

18. The method for manufacturing coke according to claim 12, wherein the interfacial tension among the kinds of coal is an interfacial tension $\gamma_{inter}$ derived from equation (2) below using the surface tension of each kind of coal:

$$\gamma_{inter} = 0.032\sigma_\gamma^2, \text{ where} \qquad (2)$$

$$\sigma_\gamma^2 = \frac{100}{100\sum_{i=1}^{n} w_i - 1}\left[\sum_{i=1}^{n}\gamma_i^2 w_i - \frac{\left(\sum_{i=1}^{n}\gamma_i w_i\right)^2}{\sum_{i=1}^{n} w_i}\right] \sum_{i=1}^{n} w_i = 1$$

$\gamma_i$: the surface tension of coal i
$w_i$: the blending ratio of coal i
$\gamma_{inter}$: the interfacial tension of a coal blend consisting of coal 1, coal 2, . . . , coal i, . . . and coal n
$\sigma_\gamma^2$: the variance of the surface tensions of all the constituent kinds of coal.

19. The method for manufacturing coke according to claim 18, wherein the blending ratio of each kind of coal is determined so that the interfacial tension $\gamma_{inter}$ is 0.03 mN/m or less.

20. The method for manufacturing coke according to claim 18, wherein a coal blend having a weighted average value of Ro of the constituent kinds of coal of 0.90% or more and 1.30% or less and a weighted average value of logMF of the constituent kinds of coal of 2.3 or more and 2.8 or less is used, where Ro is a mean maximum reflectance and MF is a Gieseler maximum fluidity.

21. The method for manufacturing coke according to claim 18, wherein the blending ratio of each kind of coal is determined so that the interfacial tension $\gamma_{inter}$ is 0.02 mN/m or less in the case of a coal blend having a weighted average value of Ro of the constituent kinds of coal of 0.90% or more and 1.30% or less and a weighted average value of logMF of the constituent kinds of coal of 2.0 or more and less than 2.3, where Ro is a mean maximum reflectance and MF is a Gieseler maximum fluidity.

22. The method for manufacturing coke according to claim 18, wherein the blending ratio of each kind of coal is determined so that the interfacial tension $\gamma_{inter}$ is 0.01 mN/m or less in the case of a coal blend containing 30 mass % or more of coal having a logMF of 1.4 or less, where MF is a Gieseler maximum fluidity.

23. A method for manufacturing coke in which a coal blend is formed by blending two or more kinds of coal and the coal blend is carbonized, the method comprising:
determining a blending ratio of each kind of coal so that at least one of interfacial tensions $\gamma_{inter}$ obtained from the equations (1) and (2) below of the coal blend is 0.03 mN/m or less:

$$\gamma_{inter} = W\Gamma W^t, \text{ where} \qquad (1)$$

$$\Gamma = \begin{bmatrix} \gamma_{11} & \gamma_{12} & \cdots & \gamma_{1j} & \cdots & \gamma_{1n} \\ \gamma_{21} & \gamma_{22} & & & & \vdots \\ \vdots & & \ddots & & & \vdots \\ \gamma_{i1} & & & \gamma_{ij} & & \gamma_{in} \\ \vdots & & & & \ddots & \vdots \\ \gamma_{n1} & \cdots & \cdots & \gamma_{nj} & \cdots & \gamma_{nn} \end{bmatrix}$$

$$\gamma_{ij} = \gamma_i + \gamma_j - 2\exp[-\beta(\gamma_i - \gamma_j)^2]\sqrt{\gamma_i\gamma_j}$$

$$\gamma_{ij} = \gamma_{ji}$$

$$W = (w_1\ w_2\ \ldots\ w_i\ \ldots\ w_n)$$

$$\sum_{i=1}^{n} w_i = 1$$

$\gamma_i$: the surface tension of coal i
$\gamma_{ij}$: the interfacial tension between coal i and coal j
$w_i$: the blending ratio of coal i
$\gamma_{inter}$: the interfacial tension of a coal blend consisting of coal 1, coal 2, . . . , coal i, . . . and coal n;

$$\sigma_\gamma^2 = \frac{100}{100\sum_{i=1}^{n} w_i - 1}\left[\sum_{i=1}^{n}\gamma_i^2 w_i - \frac{\left(\sum_{i=1}^{n}\gamma_i w_i\right)^2}{\sum_{i=1}^{n} w_i}\right] \sum_{i=1}^{n} w_i = 1$$

$\gamma_i$: the surface tension of coal i
$w_i$: the blending ratio of coal i
$\gamma_{inter}$: the interfacial tension of a coal blend consisting of coal 1, coal 2, . . . , coal i, . . . and coal n
$\sigma_\gamma^2$: the variance of the surface tensions of all the constituent kinds of coal; and
carbonizing the coal blend to form the coke,
wherein the surface tension of the coal is a surface tension obtained by heating the coal at a temperature of 350° C. or higher and 800° C. or lower, by cooling the heated coal under an inert gas atmosphere, and by performing measurement using the cooled coal.

24. The method for manufacturing coke according to claim 23, wherein a coal blend having a weighted average value of Ro of the constituent kinds of coal of 0.90% or more and 1.30% or less and a weighted average value of logMF of the constituent kinds of coal of 2.3 or more and 2.8 or less is used, where Ro is a mean maximum reflectance and MF is a Gieseler maximum fluidity.

25. The method for manufacturing coke according to claim 23, wherein the blending ratio of each kind of coal is determined so that the interfacial tension $\gamma_{inter}$ is 0.02 mN/m or less in the case of a coal blend having a weighted average value of Ro of the constituent kinds of coal of 0.90% or more and 1.30% or less and a weighted average value of logMF of the constituent kinds of coal of 2.0 or more and less than 2.3, where Ro is a mean maximum reflectance and MF is a Gieseler maximum fluidity.

26. The method for manufacturing coke according to claim 23, wherein the blending ratio of each kind of coal is determined so that the interfacial tension $\gamma_{inter}$ is 0.01 mN/m or less in the case of a coal blend containing 30 mass % or more of coal having a logMF of 1.4 or less, where MF is a Gieseler maximum fluidity.

\* \* \* \* \*